United States Patent [19]

Suzuki

[11] Patent Number: 5,231,885
[45] Date of Patent: Aug. 3, 1993

[54] METHOD FOR CHECKING MULTILAYER PRINTED WIRING BOARD

[75] Inventor: Toshiya Suzuki, Tokyo, Japan
[73] Assignee: NEC Corporation, Tokyo, Japan
[21] Appl. No.: 926,158
[22] Filed: Aug. 5, 1992
[30] Foreign Application Priority Data
　　Aug. 6, 1991 [JP] Japan .................................. 3-196358
[51] Int. Cl.$^5$ .................................................. G01L 3/02
[52] U.S. Cl. ............................. 73/862.191; 73/862.08
[58] Field of Search ................... 73/862.191, 862.192, 73/862.193, 862.29, 862.08; 33/1 BB, 286, 645; 175/40; 324/158 R

[56] References Cited

U.S. PATENT DOCUMENTS

| | | | |
|---|---|---|---|
| 4,510,446 | 4/1985 | Braun et al. | 324/158 R |
| 4,608,861 | 9/1986 | Wachtler et al. | 175/40 X |
| 4,894,606 | 1/1990 | Paur | 324/73.1 |
| 4,918,380 | 4/1990 | Paur | 324/158 R X |
| 4,958,517 | 9/1990 | Maron | 175/40 X |
| 4,985,675 | 1/1991 | Turudic | 324/158 R |
| 5,014,793 | 5/1991 | Germantown et al. | 73/862.193 X |
| 5,141,061 | 8/1992 | Henneuse | 175/40 X |

Primary Examiner—Richard E. Chilcot, Jr.
Assistant Examiner—Elizabeth L. Dougherty

[57] ABSTRACT

A multilayer printed wiring board includes a plurality of internal conductor layers located at different levels and separated from each other by an interlayer insulator layer, and each of the internal conductor layers has a clearance hole at a position different from that of the other internal conductor layers. The multilayer printed wiring board is perforated at an expected position of the clearance hole of a selected internal conductor layer with a rotating drill bit, while continuously measuring a torque of a motor driving the rotating drill bit and an axial displacement of the rotating drill bit. A position of the internal conductor layers along a sample hole perforated in the multilayer printed wiring board is determined on the basis of the measured torque of the rotating drill bit and the axial displacement of the rotating drill bit. Thus, a mistake of the order stacking the internal conductor layers, and a positional deviation of each internal conductor layer in comparison with the other internal conductor layers, can be found at an early stage of a manufacturing of the multilayer printed wiring board.

3 Claims, 5 Drawing Sheets

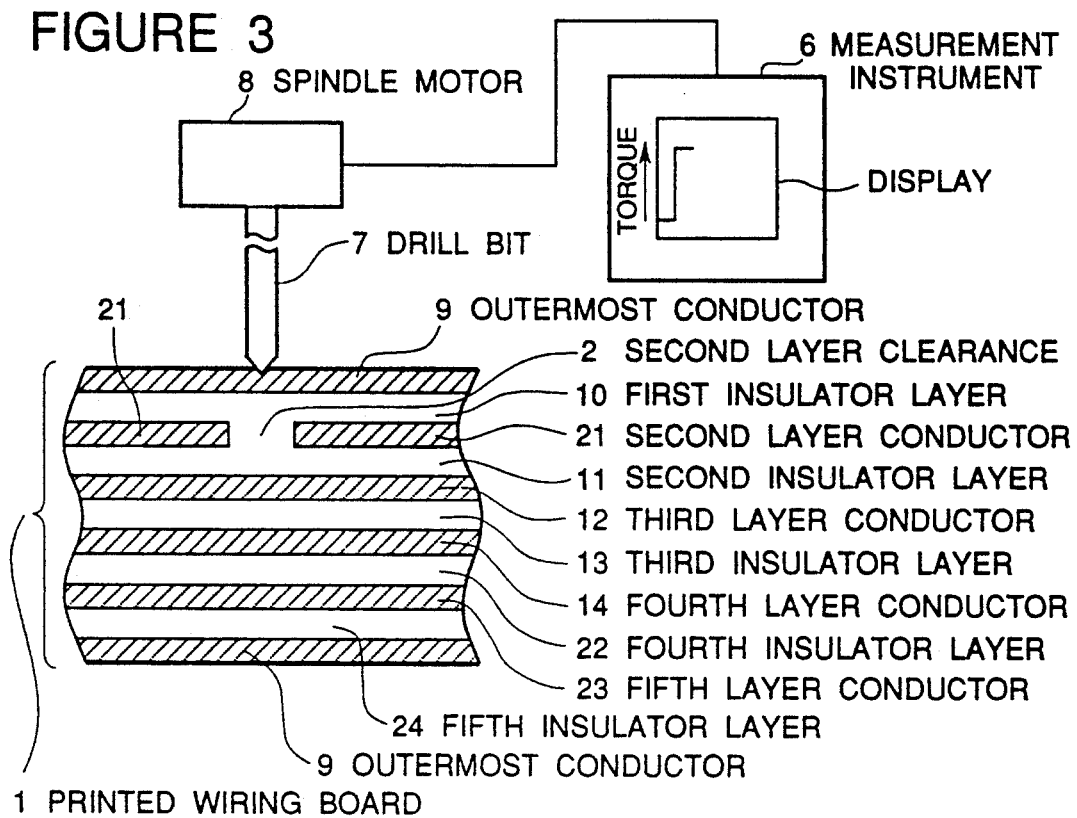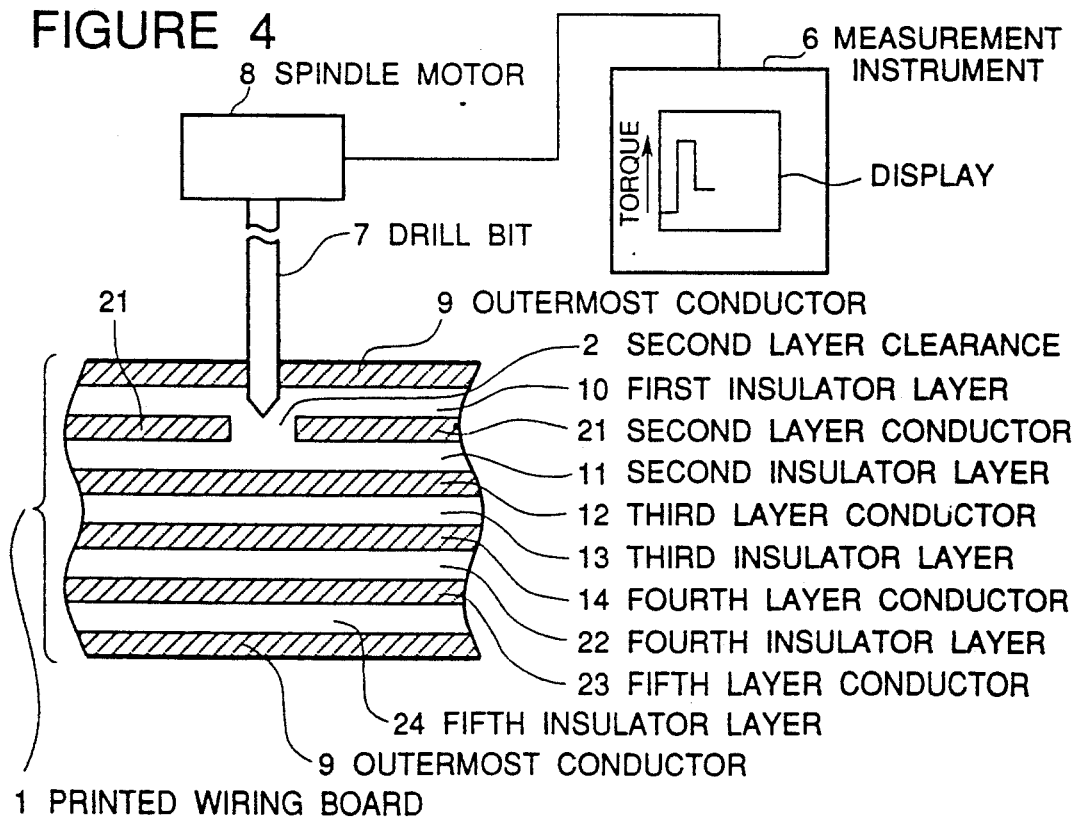

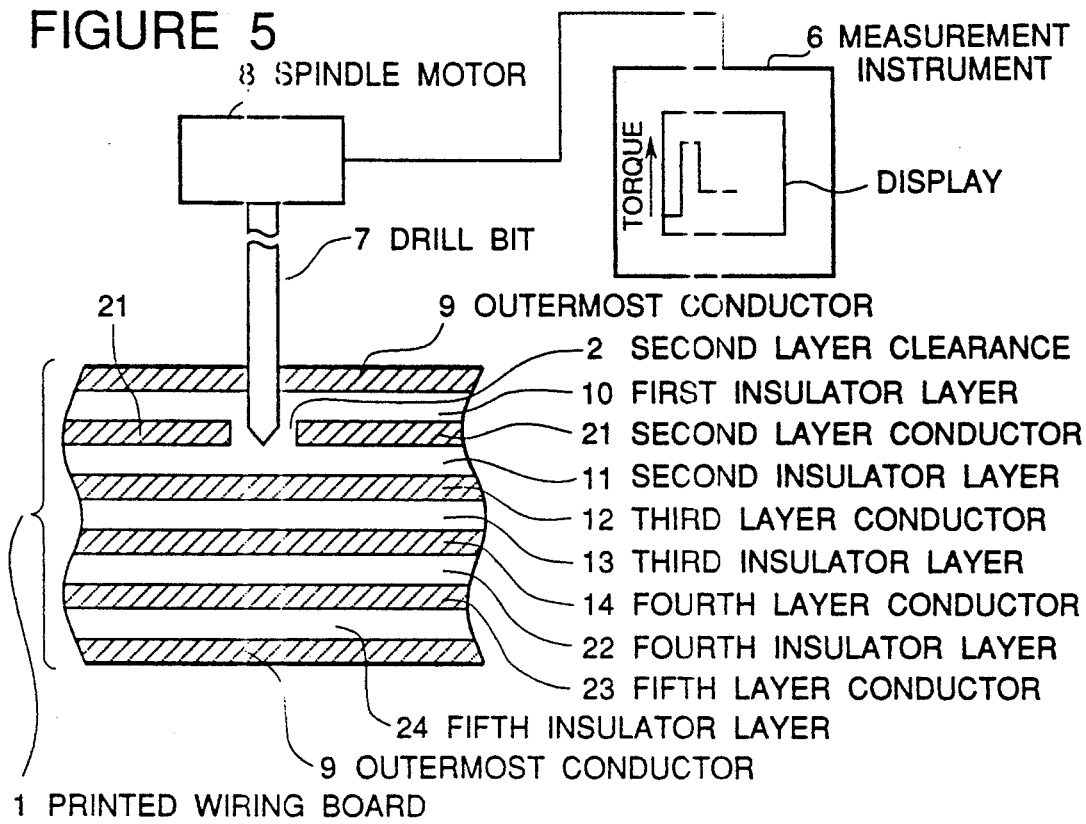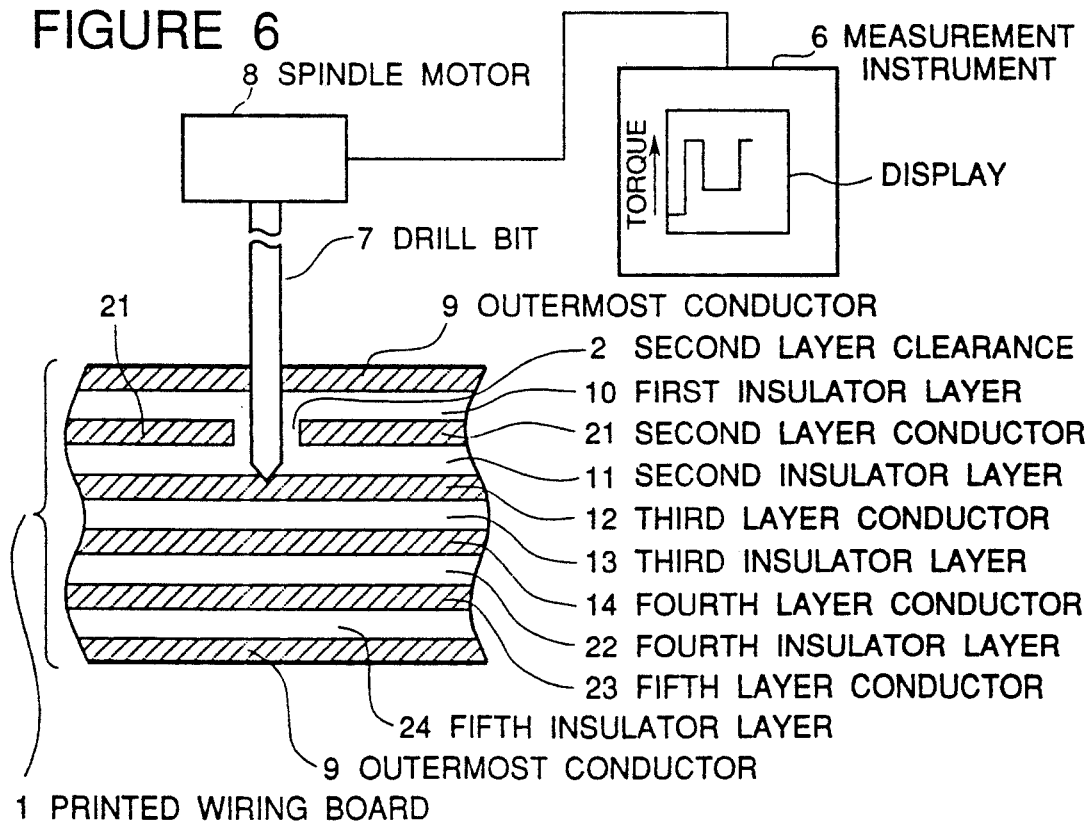

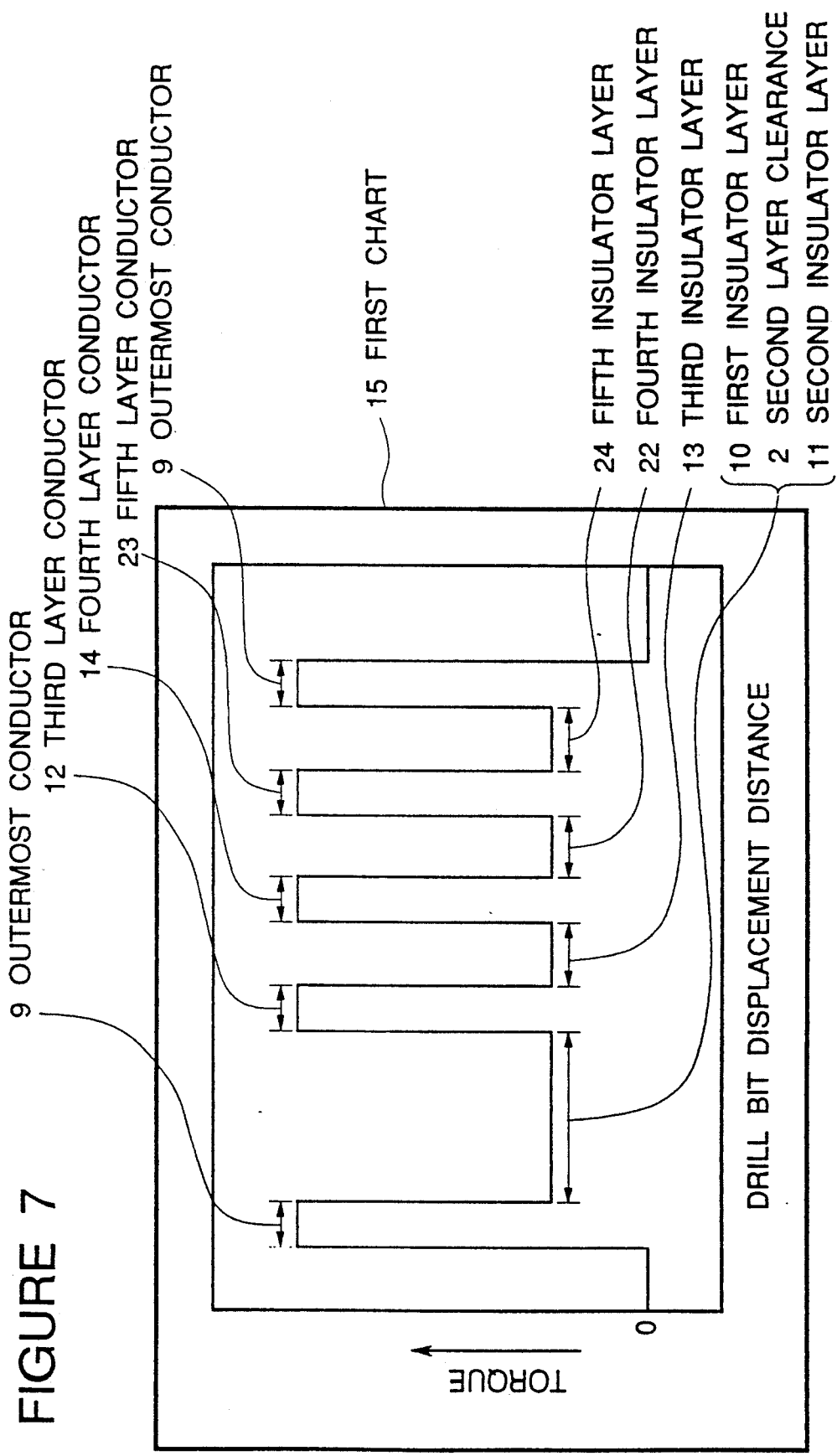

METHOD FOR CHECKING MULTILAYER PRINTED WIRING BOARD

BACKGROUND OF THE INVENTION

1. Field of the Invention

The present invention relates to a method for checking a multilayer printed wiring board, and more specifically to a method for checking a position of each internal conductor layer within the multilayer printed wiring board.

2. Description of related art

In the prior art, a position of each internal conductor layer within a multilayer printed wiring board has been checked by observing a section of a test piece taken out at the time of conducting an outline trimming (outline machining) of the printed wiring board, or by examining, at the time of the outline trimming, a pattern which is provided on outline trimming lines of the printed wiring board and which corresponds to a pattern of internal conductor layers. Otherwise, no checking has been performed.

In any case, the conventional checking has been ordinarily conducted just before to a final stage of a process of manufacturing the printed wiring board. More specifically, the conventional checking has been performed when the outline trimming is conducted by a punching or a router machining after required circuits have been completed and a protection coating has been deposited. On the other hand, a recent increased number of internal layers in the multilayer printed wiring board and a today's high added value of the multilayer printed wiring board require increased days for manufacturing and an increased manufacturing cost. Therefore, disposal of the multilayer printed wiring board as being defective at a later stage of the manufacturing process will cause various series problems, for example, a delayed time of delivery due to re-manufacturing, and an increased miss or failure cost.

SUMMARY OF THE INVENTION

Accordingly, it is an object of the present invention to provide a method for checking a multilayer printed wiring board which has overcome the above mentioned defect of the conventional one.

Another object of the present invention is to provide a method for checking a position of each internal conductor layer within a multilayer printed wiring board, which method can be conducted at an early stage of a multilayer printed wiring board manufacturing process, so that the miss or failure cost can be decreased.

The above and other objects of the present invention are achieved in accordance with the present invention by a method for checking a multilayer printed wiring board including a plurality of internal conductor layers located at different levels and separated from each other by an interlayer insulator layer, each of the internal conductor layers having a clearance hole at a position different from that of the other internal conductor layers, the method comprising the step of perforating the multilayer printed wiring board at an expected position of the clearance hole of a selected internal conductor layer with a rotating drill bit while continuously measuring a torque of the rotating drill bit and an axial displacement of the rotating drill bit, and determining position of the internal conductor layers along a sample hole perforated in the multilayer printed wiring board on the basis of the measured torque of the rotating drill bit and the axial displacement of the rotating drill bit.

The above and other objects, features and advantages of the present invention will be apparent from the following description of preferred embodiments of the invention with reference to the accompanying drawings.

BRIEF DESCRIPTION OF THE DRAWINGS

FIGS. 2 to 6 are diagrammatic partial sectional views for illustrating different steps of the embodiment of the method in accordance with the present invention;

FIG. 7 illustrates a display of the measurement instrument in the case that a sample hole is perforated at a position of a clearance hole previously formed in a second conductor layer of the multilayer printed wiring board.

DESCRIPTION OF THE PREFERRED EMBODIMENTS

Figure 1:
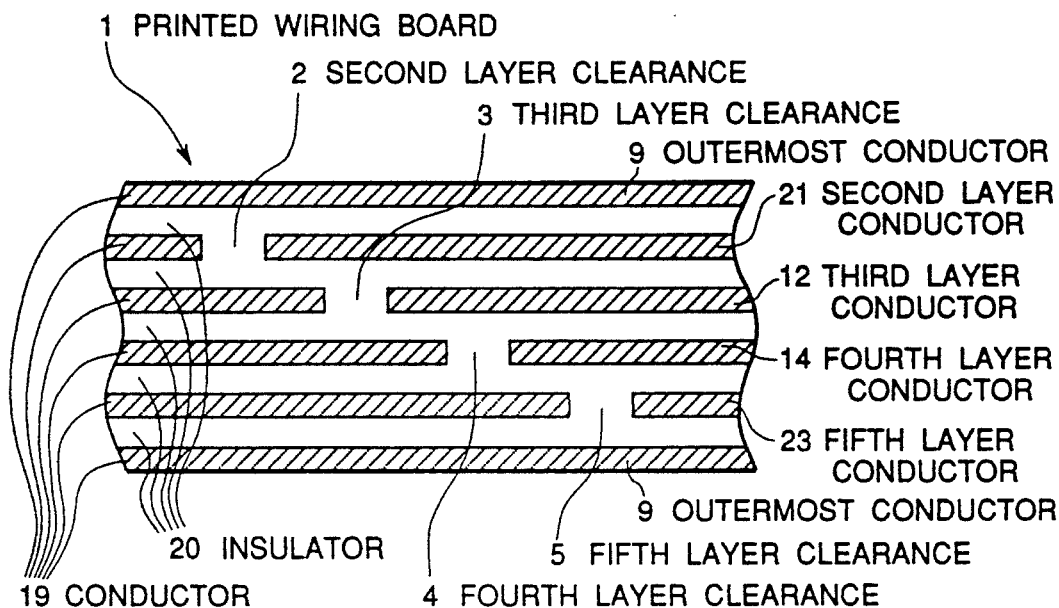
FIG. 1 is a diagrammatic partial sectional view of a multilayer printed wiring board used in an embodiment of the method in accordance with the present invention.

Referring to FIG. 1, there is shown a diagrammatic partial sectional view of a six-layer printed wiring board used in an embodiment of the method in accordance with the present invention.

The shown six-layer printed wiring board, generally designated with Reference Numeral 1, has six conductor layers 19 located at different levels and separated from each other by an interlayer insulator layer 20. Each of four internal conductor layers 21, 12, 14 and 23 of the six conductor layers 19 has a clearance hole 2, 3, 4 or 5 at a position different from that of the other internal conductor layers, as shown in FIG. 1. Namely, the second layer clearance hole 2, the third layer clearance hole 3, the fourth layer clearance hole 4 and the fifth layer clearance hole 5 are staggered or shifted from one another. On the other hand, a pair of outermost conductor layers 9 have no clearance hole.

The six conductor layers 19 are formed of, for example, a copper foil, and the interlayer insulator layers 20 are formed of a prepreg. The above mentioned six-layer printed wiring board 1 can be formed as follows: Copper foils forming the four internal conductor layers are selectively etched so that the clearance holes 2, 3, 4 and 5 are formed in the copper foils, respectively. The four copper foils having the clearance holes 2, 3, 4 and 5 are stacked on each other with a prepreg (forming the interlayer insulator layer 20) being interposed between each pair of adjacent copper foils, and then, a copper foil having no clearance hole is stacked through another prepreg on each surface of a stacked body of the four copper foils. The stacked structure thus formed is heat-pressed so as to form a molded stacked structure, namely, the six-layer printed wiring board 1.

Now, an embodiment in accordance with the present invention of the method for checking a multilayer printed board will be described with reference to FIGS. 2 to 6, which are diagrammatic partial sectional views for illustrating different steps of the method for checking a multilayer printed wiring board.

In FIGS. 2 to 6, Reference Numeral 7 designates a drill bit, which is fixed to a rotating chuck (not shown)

driven by a spindle motor 8. This spindle motor 8 is configured to be displaced along an axial direction of the drill bit 7 so as to cause the drill bit 7 to perforate the printed wiring board 1. The spindle motor 8 is coupled to a measurement instrument 6, which continuously measures a torque of the spindle motor 8 changing with an axial displacement of the spindle motor and hence the drill bit, and records and displays the measured torque and the axial displacement.

In the process illustrated in FIGS. 2 to 6, a sample hole is perforated through the printed wiring board 1 at a position of the second layer clearance hole 2 formed in the second layer conductor 21.

Figure 2:
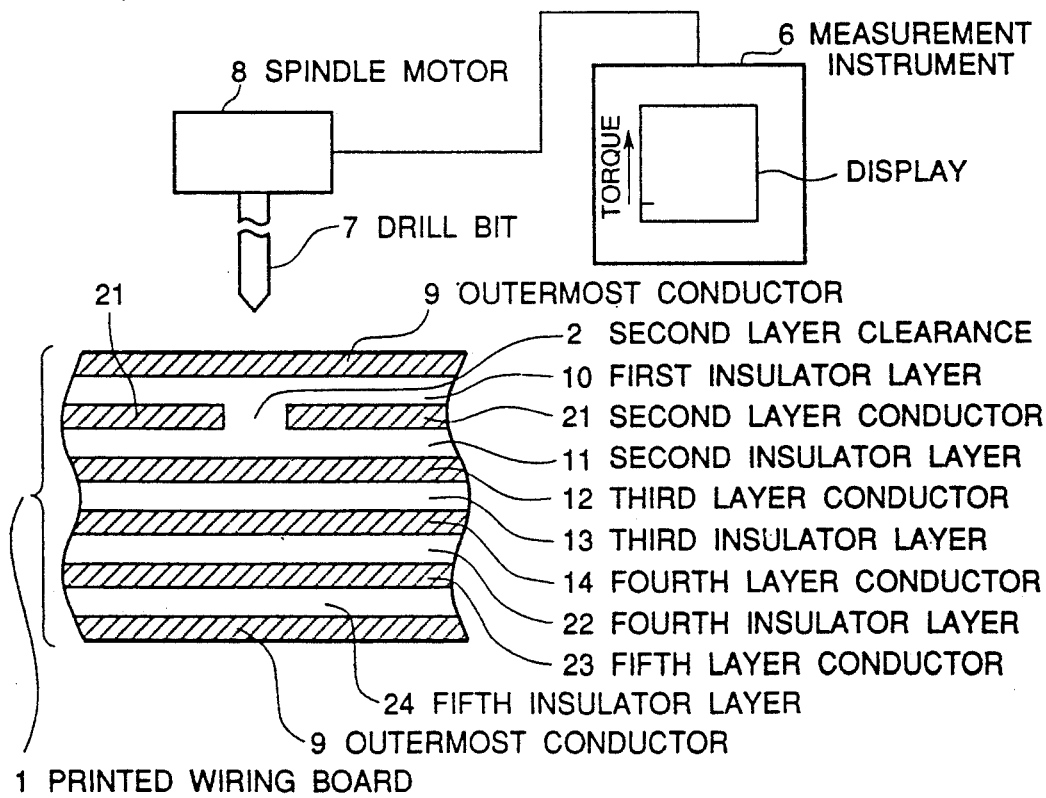

FIG. 2 shows a condition in which the drill bit 7 has not yet been forced onto the printed wiring board 1. Namely, the axial displacement of the spindle motor is zero, and therefore, the drill bit 7 has not yet contacted to the printed wiring board 1. In this condition, the measurement instrument 6 indicates that no torque acts on the spindle motor 8.

FIG. 3 shows a condition in which the drill bit 7 is forced onto the printed wiring board 1 and is brought int contact with the outermost conductor layer 9. Since the drill bit 7 is drilling the copper foil of the outermost conductor layer 9, the measurement instrument indicates that a large torque acts on the spindle motor 8. This large torque continues until the outermost conductor layer 9 is completely perforated by the drill bit 7.

FIG. 4 shows a condition in which the drill bit 7 is drilling the prepreg of the first insulator layer 10 after the outermost conductor layer 9 has been completely perforated. At this time, the measurement instrument 6 indicates that a decreased torque acts on the spindle motor 8. This decreased torque continues until the drill bit 7 starts to drill another conductor layer, again. From this decrease of the torque, it can be known that the outermost conductor layer 9 has been completely perforated, namely, the drill bit 7 has completely passed through the outermost conductor layer 9.

FIG. 5 shows a condition in which the drill bit 7 is drilling the second clearance hole 2 formed in the second layer conductor 21. Since the second clearance hole 2 is filled with the same material as the first insulator layer 10, the torque acting on the spindle motor 8 does not change.

FIG. 6 shows a condition in which the drill bit 7 is drilling the third layer conductor 12 after the second clearance hole 2 and the second insulator layer 11 have been completely perforated. Since the drill bit 7 is drilling the conductor layer, the measurement instrument 6 indicates that a large torque acts on the spindle motor 8, again.

Similarly, the third insulator layer 13, the fourth layer conductor 14, the fourth insulator layer 22, the fifty layer conductor 23, the fifth insulator layer 24, and the bottom side outermost conductor 9 are sequentially perforated by the drill bit 7, so that a sample through-hole is formed in the printed wiring board 1. In this process, each time the drill bit 7 drills the conductor layer, a large torque acts on the spindle motor 8. Accordingly, a torque chart 15 as shown in FIG. 7 is obtained. In the chart of FIG. 7, the axis of ordinate shows the torque, and the axis of abscissas shows the axial displacement of the drill bit 7. Peaks and valleys of the torque correspond to the respective layers indicated by legends given in FIG. 7.

It will be understood that the position and the number of the internal conductor layers can be roughly discriminated from the number of the peaks of the torque and the width of each valley of the torque.

Figure 8:
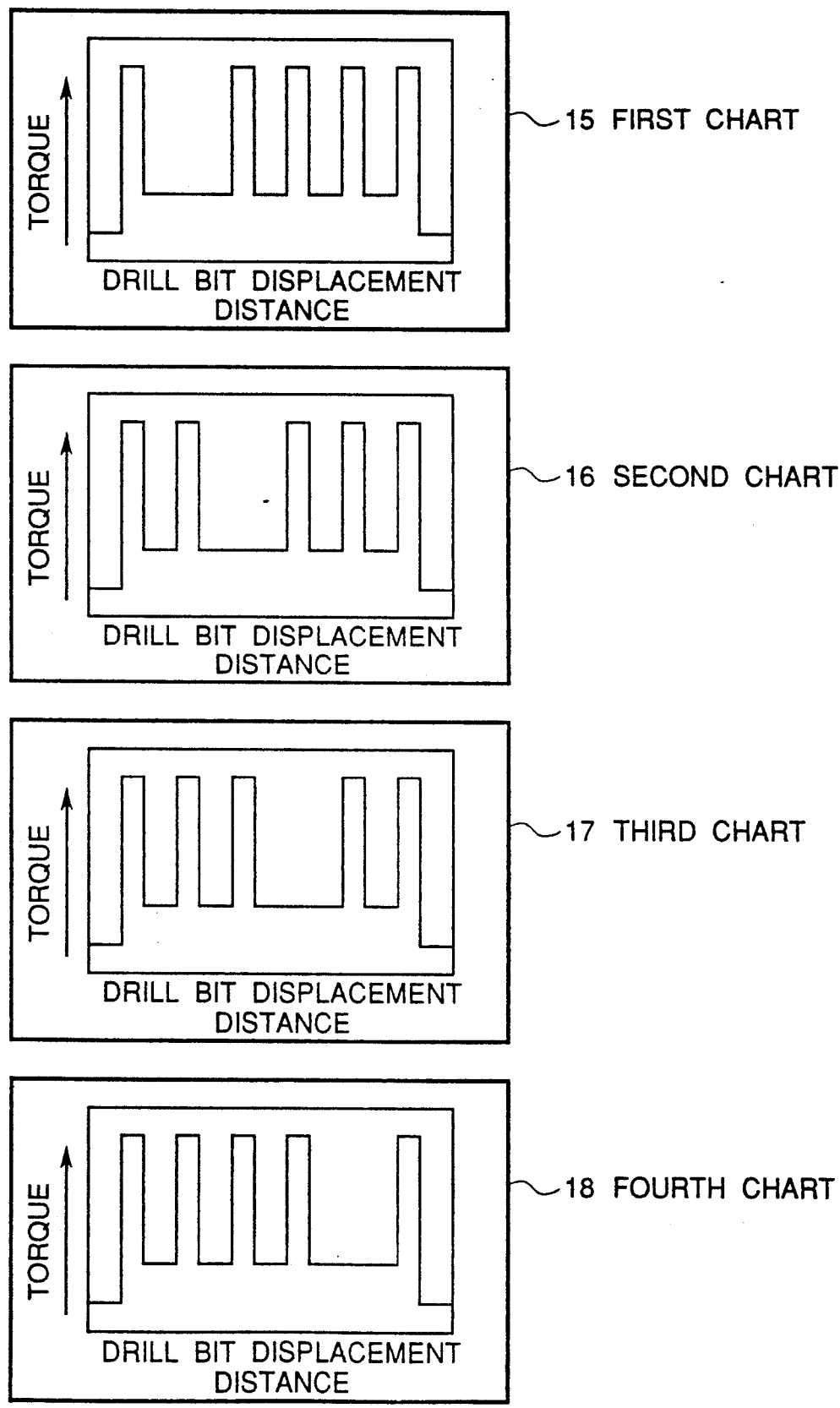
FIG. 8 illustrates various displays of the measurement instrument in the case that a sample hole is perforated at different positions in different conductor layers of the multilayer printed wiring board.

Referring to FIG. 8, there is shown four different torque charts obtained by drilling the six-layer printed wiring board. A first torque chart 15 corresponds to the example explained with reference to FIGS. 2 to 7, namely, the case in which a sample hole is perforated in the printed wiring board 1 at a position of the second layer clearance hole 2 formed in the second layer conductor 21. A second torque chart 16 corresponds to the case in which a sample hole is perforated in the printed wiring board 1 at a position of the third layer clearance hole 3 formed in the third layer conductor 12. A third torque chart 17 corresponds to the case in which a sample hole is perforated at a position of the fourth layer clearance hole 4, and a fourth torque chart 18 corresponds to the case in which a sample hole is perforated at a position of the fifth layer clearance hole 5.

If the four torque charts 15 to 18 are arranged with their drill bit displacement in matching with each other as shown in FIG. 8, a wide valley of each chart corresponds to one of the peaks of the other charts. Namely, the four internal conductor layers are precisely arranged.

As seen from the above, according to the method of the present invention, a mistake of the order stacking the internal conductor layers, and a positional deviation of each internal conductor layer in comparison with the other internal conductor layers, can be easily found at a small-hole drilling step, which is remarkably earlier than the outline trimming step in a process for manufacturing the multilayer printed wiring board.

The invention has thus been shown and described with reference to the specific embodiments. However, it should be noted that the present invention is in no way limited to the details of the illustrated structures but changes and modifications may be made within the scope of the appended claims.

I claim:

1. A method for checking a multilayer printed wiring board including a plurality of internal conductor layers located at different levels and separated from each other by an interlayer insulator layer, each of said internal conductor layers having a clearance hole at a position different from that of the other internal conductor layers, the method comprising the step of performing said multilayer printed wiring board at an expected position of said clearance hole of a selected internal conductor layer with a rotating drill bit while continuously measuring a torque of said rotating drill bit and an axial displacement of said rotating drill bit, and determining position of said internal conductor layers along a sample hole perforated in said multilayer printed wiring board on the basis of the measured torque of said rotating drill bit and the axial displacement of said rotating drill bit.

2. A method claimed in claim 1 wherein said perforation of said multilayer printed wiring board is repeatedly performed at different positions corresponding to respective clearance holes of said internal conductor layers.

3. A method claimed in claim 1 wherein said rotating drilling bit is driven by a spindle motor and a torque of said spindle motor is measured.

* * * * *